United States Patent [19]

Hardman et al.

[11] 4,065,507
[45] Dec. 27, 1977

[54] PREPARATION OF METHACRYLIC DERIVATIVES FROM TERTIARY BUTYL-CONTAINING COMPOUNDS

[75] Inventors: Harley F. Hardman, Lyndhurst; James L. Callahan, Wooster; Robert K. Grasselli, Chagrin Falls, all of Ohio

[73] Assignee: Standard Oil Company, Cleveland, Ohio

[21] Appl. No.: 711,014

[22] Filed: Aug. 2, 1976

[51] Int. Cl.$^2$ .............................................. C07C 45/16
[52] U.S. Cl. .............................. 260/604 R; 260/603 C
[58] Field of Search ........ 260/603 R, 603 HF, 603 C, 260/604 R, 603

[56] References Cited

U.S. PATENT DOCUMENTS

| | | | |
|---|---|---|---|
| 3,470,239 | 9/1969 | Russell | 260/603 R |
| 3,716,497 | 2/1973 | Courty | 260/603 HF |
| 3,825,502 | 7/1974 | Takenaka et al. | 260/604 R |
| 3,972,920 | 8/1976 | Ishii et al. | 260/531 R |

*Primary Examiner*—James O. Thomas, Jr.
*Assistant Examiner*—W. B. Lone
*Attorney, Agent, or Firm*—Evelyn R. Kosman; Herbert D. Knudsen; Larry W. Evans

[57] ABSTRACT

The present invention relates to a process for the conversion of tertiary-butyl-containing compounds to methacrylic derivatives, and more particularly to a process for the conversion of tertiary-butyl-containing compounds selected from the group consisting of alkyl tertiary-butyl ethers, tertiary-butyl alcohol, isobutylene dimer (2,2,4-trimethylpentene) and isobutylene trimer, to methacrolein, methacrylic acid or methacrylonitrile.

5 Claims, No Drawings

PREPARATION OF METHACRYLIC DERIVATIVES FROM TERTIARY BUTYL-CONTAINING COMPOUNDS

BACKGROUND OF THE INVENTION

Isobutylene, the major source of tertiary-butyl groups, is produced primarily by catalytic cracking of gas oils which yields a mixture of butane and butylenes. In commercial processes, it is the common practice to separate isobutylene from other $C_4$-hydrocarbons obtained in the cracking process by absorption in sulfuric acid. The separation of isobutylene from the other compounds in the acid solution is costly. It is therefore economically advantageous to use a mixed feed containing isobutylene or a reaction product of isobutylene formed as a means for separating isobutylene from a mixture of $C_4$-hydrocarbons, as a starting material for the present process. For example, in the course of the isobutylene separation of sulfuric acid adsorption, there is formed approximately 5–10% of di-isobutylene and tri-isobutylene. The use of an isobutylene mixture of this nature as a starting material in the present process offers a distinct cost advantage over the use of pure isobutylene.

The reaction of isobutylene to form butyl ethers represents a different means for separating isobutylene from a mixed $C_4$-stream, and the ether may be another source of a low cost starting material. Another source of the tertiary butyl group for the starting material of the present invention is tertiary-butyl alcohol which may be available as a low cost by-product from other processes, such as a by-product of epoxidation with tertiary-butyl hydroperoxide.

It is therefore an outstanding advantage of the present process that the $C_4$-hydrocarbon mixture resulting from the acid absorption or other tertiary-butyl group sources such as isobutylene derivatives, can be directly converted to methacrolein, methacrylic acid or methacrylonitrile without the need for separate regeneration and purification of isobutylene. In the course of the reaction of the present invention, the catalyst compositions utilized also promote the formation of isobutylene from the tertiary-butyl compounds employed in the reaction, and the isobutylene thus formed can be selectively oxidized or ammoxidized to the corresponding unsaturated aldehyde and acid or the unsaturated nitrile, respectively.

SUMMARY OF THE INVENTION

It is the object of this invention to produce methacrolein, methacrylic acid or methacrylonitrile by the direct selective oxidation or ammoxidation of a compound selected from the group consisting of tertiary-butyl alcohol, alkyl tertiary-butyl ether wherein the alkyl group contains from 1 to 4 carbon atoms, isobutylene dimer, isobutylene trimer and mixtures of the dimer and/or trimer with isobutylene, in the presence of molecular oxygen or a mixture of molecular oxygen and ammonia, optionally in the presence of steam, by passing said reaction mixture over a catalyst at an elevated temperature wherein said catalyst has a composition represented by the formula:

$$A_a C_c Fe_e Bi_f D_d Mo_g O_x$$

wherein

A is an alkali metal, barium, strontium, thallium, indium, silver, copper or mixtures thereof;
C is nickel, cobalt, magnesium, zinc, manganese, cadmium, calcium or their mixtures;
D is phosphorus, antimony, germanium, chromium, thorium, tin, niobium, praseodymium, tungsten, boron, zirconium, cerium, arsenic or their mixtures; and
wherein
  $a$ is a number from 0 to 3;
  $c$ is a number from 0.001 to 12;
  $d$ is a number from 0.0 to 3;
  $e$ and $f$ are each a number from 0.01 to 12;
  $g$ is 12; and
  $x$ is the number of oxygens required to satisfy the valence requirements of the other elements present.

Preferred catalyst compositions are those wherein A is an alkali metal such as, potassium, rubidium or cesium; C is nickel or cobalt or both, and D is phosphorous or antimony or both.

The catalyst of the invention may be employed in the supported or unsupported form. In a commercial reactor, it might be desirable to use a catalyst support which may constitute from 3 percent to 99 percent, and preferably between 5 percent and 95 percent by weight of the finished catalyst. Any known catalyst support such as alumina, pumice, silicon carbide, zirconia, titania, silica, alumina-silica, and the inorganic phosphates, silicates, aluminates, borates and carbonates that are stable under the reaction conditions may be used.

The catalysts of the invention are prepared by techniques known in the art. These techniques include the coprecipitation of soluble salts. The metal oxides can be blended together, or can be formed separately and then blended, or formed separately or together in situ. Promoter oxides are preferably incorporated into the bismuth-molybdenum-iron base catalyst by blending into the gel before calcining or by blending into the oven-dried base catalyst before calcining. A preferred manner of incorporating promoter elements is by choosing a water-soluble salt of the promoter element, forming an aqueous solution of the salt, and mixing the solution with a solution or a suspension of the base elements or salts thereof. Optionally, the promoter elements may be incorporated by the use of soluble complex salts or compounds with the desired base elements which upon calcination will yield the desired ratio of the elements in the finished catalyst.

More specific information on the preparation of the catalysts is given in the Specific Embodiment.

OXIDATION TO ALDEHYDES & ACIDS

In the process of the present invention a mixture of the feed and molecular oxygen, optionally in the presence of steam or other diluents, is contacted with a catalyst of the above composition, at an elevated temperature of about 200°–600° C, for a contact time sufficient to convert the feed to the unsaturated aldehyde or acid. The contact time may vary widely, from 1 to 20 seconds or more. The reaction can be conducted under atmospheric, superatmospheric or subatmospheric pressures. However, in general, pressures near atmospheric, i.e., −10 to 100 psig are preferred.

Any source of oxygen may be employed in this process, and for economic reasons, it is preferred that air be employed as the source of oxygen. Where it is desirable to produce unsaturated aldehydes or acids the molar ratio of oxygen to the starting compound may range between 0.5:1 to 10:1 with the preferred ratio being in the range of from about 1:1 to about 5:1. The addition of water to the reaction mixture has a beneficial influence on the course of the reaction in that it improves the conversion and the yields of the desired product. Accordingly, it is preferred to include water in the reaction mixture. Generally, a ratio of starting compound to water in the reaction mixture of from 1:0.5 to 1:10 will give very satisfactory results, and a ratio of from 1:0.75 to 1:6 has been found to be most desirable. The water, of course, will be in the vapor phase during the reaction.

Inert diluents, such as nitrogen and carbon dioxide, may be present in the reaction mixture.

OXIDATION TO NITRILES

The reactants employed are the same as those employed in the production of aldehydes and acids, above, plus ammonia. In its preferred aspect, the process comprises contacting a mixture comprising the starting compound, ammonia and oxygen with the catalyst at an elevated temperature and at atmospheric or near atmospheric pressure.

Again, any source of oxygen may be employed in this process, and it is preferred that air be employed as the source of oxygen. From a purely technical viewpoint, relatively pure molecular oxygen will give equivalent results. The molar ratio of oxygen to the starting compound in the feed to the reaction vessel should be in the range of 0.5:1 to 10:1 and a ratio of about 1:1 to 5:1 is preferred. Diluents such as nitrogen and the oxides of carbon may be present in the reaction mixture without deleterious effect.

The molar ratio of ammonia to the starting material in the feed to the reaction may vary between about 0.5:1 to 5:1. There is no real upper limit for the ammonia-starting compound ratio, but there is generally no reason to exceed the 5:1 ratio. At ammonia-starting compound ratios appreciably less than the stoichiometric ratio of 1:1, various amounts of oxygenated derivates will be formed.

Significant amounts of unsaturated aldehydes and even unsaturated acids as well as nitriles will be obtained at ammonia-starting compound ratios substantially below 1:1, i.e., the range of 0.15:1 to 0.75:1. Outside the upper limit of this range only insignificant amounts of aldehydes and acids will be produced, and only small amounts of nitriles will be produced at ammonia-starting compound ratios below the lower limit of this range. It is generally possible to recycle any of the unreacted starting compound and unconverted ammonia.

We have found that in many cases water in the mixture fed to the reaction vessel improves the selectively of the reaction and yield of nitrile. However, reactions not including water in the feed are not to be excluded from this invention, inasmuch as water is formed in the course of the reaction. Sometimes it is desirable to add some water to the reaction mixture, and in general, molar ratios of added water to the starting material, when water is added, on the order of 1:1 to 4:1 are particularly desirable. However higher ratios may be employed, i.e., ratios of up to about 10:1 are feasible.

The reaction is carried out at a temperature within the range from about 250° to about 600° C. The preferred temperature range is from about 350° to 500° C.

The pressure at which the reaction is conducted is not critical, and the reaction should be carried out at about atmospheric pressure or pressures up to about 5 atmospheres.

The apparent contact time is an important variable, and contact time in the range of from 0.1 to about 20 seconds may be employed. The optimum contact time will, of course, vary, depending upon the compound being treated, but in general, a contact time of from 1 to 15 seconds is preferred.

In general, any apparatus of the type suitable for carrying out oxidation reactions in the vapor phase may be employed in the execution of this process. The processes may be conducted either continuously or intermittently. The catalyst bed may be a fixed-bed employing a large particulate or pelleted catalyst, or in the alternative, a so-called "fluidized" bed of catalyst may be employed.

The reactor may be brought to the reaction temperature before or after the introduction of the reaction feed mixture. However, in a large scale operation, it is preferred to carry out the process in a continuous manner, and in such a system the recirculation of the unreacted starting material is contemplated.

The products of the reaction may be recovered by any of the methods known to those skilled in the art. One such method involves scrubbing the effluent gases from the reactor with cold water or an appropriate solvent to remove the products of the reaction. In the recovery of nitrile products it may be desirable to employ acidified water to absorb the products of reaction and neutralize unconverted ammonia. The ultimate recovery of the products may be accomplished by conventional means, such as by distillation or solvent extraction.

The examples disclosed in the Specific Embodiment are representative of the process conditions and catalyst compositions that are suitable for the process of this invention, however, the scope of the invention is not to be limited by these examples.

SPECIFIC EMBODIMENT

EXAMPLE 1

Catalyst Preparation:
$82.5\%\text{-}K_{0.07}Ni_{2.5}Co_{4.5}Fe_3BiP_{0.5}MO_{12\ O50}\text{-}17.5\%\ SiO_2$ 47.5 parts of ammonium heptamolybdate were dissolved in 105.7 parts of warm distilled water and 1.29 parts of 85% $H_3PO_4$ were added, followed by 6.75 parts of Aerosil 200 silica. There were added, in succession, solutions of (a) 29.4 parts $Co(NO_3).6H_2O$ and 16.3 parts $Ni(NO_3).6H_2O$ in 7.5 parts distilled water, (b) 27.2 parts $Fe(NO_3)_3.9H_2O$ in 5 parts distilled water, (c) 10.9 parts $Bi(NO_3)_3.5H_2O$ and 1.5 parts $HNO_3$ in 10.9 parts distilled water, (d) 0.16 parts $KNO_3$ in 0.33 parts distilled water, and (e) 6.4 parts of Aerosil 200 silica.

The resulting slurry was spray dried and the resulting powder calcined at 274° – 288° C. It was then mixed with 1% graphite and tabletted. The tablets were then calcined for 5 hours at 560° C.

A feed mixture of methyl-tertiary-butyl ether, air and water in a molar ratio of 1:10:4, respectively was contacted with the above catalyst at a temperature of 371° C for a contact time of 3 seconds.

The activity of the catalyst was determined using a fixed-bed microreactor composed of a feed induction system, a molten salt bath furnace, a scrubber and a vapor phase chromatograph. The reactor was constructed from a 5 inch length of pipe having a ⅜ inch I.D., and a catalyst capacity of approximately 5 cc of catalyst.

The catalyst employed had a particle size of 10–20 mesh. The reaction product obtained from the oxidation reaction was absorbed in a water scrubber. An aliquot of the scrubber liquid was subsequently injected into a Hewlett Packard gas chromatograph, Model No. 5750, for analysis. The chromatograph contained a Porapak-Q column.

EXAMPLE 2

The same catalyst composition and reaction conditions of Example 1 were employed in this example with the exception that isobutylene dimer was employed as the feed in place of methyl-tertiary-butyl ether.

EXAMPLE 3

Catalyst Preparation: 80% - $Cs_{0.5}Ni_{2.5}Co_{4.5}Fe_3Bi_1Sb_{0.5}Mo_{12}O_{50}$.-20% $SiO_2$ 58.8 g $(NH_4)_6Mo_7O_{24}\cdot H_2O$ in 100 cc of hot $H_2O$ were added to a solution of 20.4 g $Ni(NO_3)_2\cdot 6H_2O$, 36.7 g $Co(NO_3)_2\cdot 6 H_2O$, 33.9 g $Fe(NO_3)_3\cdot 9H_2O$, 13.6 g $Bi(NO_3)_3\cdot 5H_2O$, and 1.7 g $Sb_2O_3$ in 200 cc of water and 20 cc of concentrated $HNO_3$.

50 grams Nalco 40% $SiO_2$ solution was added and the slurry was evaporated to a paste and dried at 49° C overnight, calcined 4 hours at 427° C, then 5 hours at 593° C.

Methyl-tertiary butyl ether was contacted with the above catalyst under the same reactant ratios and reaction conditions as employed in Example 1.

EXAMPLE 4

Methyl-tertiary-butyl ether was ammoxidized in the same reactor as in Example 1 in the presence of the catalyst composition shown in Example 3. A reaction mixture consisting of methyl-tertiary butyl ether, air, water and ammonia in the molar ratio of 1/14/3.5/2.4, respectively, was contacted with the catalyst of Example 3 for 3 seconds at a temperature of 399° C.

The ammoxidation product was absorbed in a water-hydrochloric acid scrubber solution and analyzed in the same manner as in Example 1.

The conversions obtained utilizing the various feeds and catalyst compositions described in the invention are summarized in Table 1. In these experiments, the results are reported as:

Single Pass Yield, % =

-continued
$$\frac{\text{Moles of desired product recovered}}{\text{Moles of compound in the feed}} \times 100$$

The conversions obtained in Experiments 1 to 4 and summarized in Table 1 substantiate the unexpectedly high per pass conversions of the various tertiary butyl-containing compounds to methacrolein and methacrylonitrile are realized.

TABLE I

| EX. | STARTING COMPOUND | CATALYST | % Per Pass Conversion To: | | |
|---|---|---|---|---|---|
| | | | Methacrolein | Methacrylonitrile | Isobutylene |
| 1 | Me-t-Butyl Ether | 82.5%-$K_{0.07}Ni_{2.5}Co_{4.5}Fe_3BiP_{0.5}Mo_{12}O_{50}$ 17.5% $SiO_2$ | 27.1 | — | 21.6 |
| 2 | Isobutylene dimer | " | 5.2 | — | 13.6 |
| 3 | Me-t-Butyl Ether | 80%-$Cs_{0.5}Ni_{2.5}Co_{4.5}Fe_3BiSb_{0.5}Mo_{12}O_{50}$ -20% $SiO_2$ | 73.0 | — | 4.0 |
| 4 | Me-t-Butyl Ether | " | 9.2 | 60.8 | 0 |

We claim:

1. A process for producing methacrolein by the oxidation of a tertiary butyl-containing compound selected from the group consisting of tertiary-butyl alcohol, alkyl tertiary-butyl ether wherein the alkyl group contains from 1 to 4 carbon atoms, isobutylene dimer, isobutylene trimer and mixtures of isobutylene dimer and/or isobutylene trimer with isobutylene, in the presence of molecular oxygen and optionally in the presence of steam, at a temperature in the range of from about 200° to 600° C, and in the presence of a catalyst having the formula:

$$A_a C_c Fe_e Bi_f D_d Mo_g O_x$$

wherein

A is an alkali metal, barium, strontium, thallium, indium, silver, copper, or mixtures thereof;

C is nickel, cobalt, magesium, zinc, manganese, cadmium, calcium, or mixtures thereof;

D is phosphorus, antimony, germanium, chromium, thorium, tin, niobium, praseodymium, tungsten, boron, zirconium, cerium, arsenic or mixtures thereof; and wherein $a$ is a number from 0 to 3;

$c$ is a number from 0.001 to 12;

$d$ is a number from 0 to 3;

$e$ and $f$ are each a number from 0.01 to 12;

$g$ is 12; and $x$ is the number of oxygens required to satisfy the valence requirements of the other elements present.

2. The process in claim 1 wherein the tertiary butyl-containing-compound is an alkyl tertiary-butyl ether wherein the alkyl group contains from 1 to 4 carbon atoms.

3. The process in claim 1 wherein the tertiary-butyl-containing compound is tertiary-butyl alcohol.

4. The process in claim 1 wherein the tertiary-butyl-containing-compund is isobutylene dimer.

5. The process in claim 1 wherein A in the catalyst formula is potassium, rubidium or cesium, C is nickle or cobalt or both and D is antimony or phosphorus or both.

* * * * *